US011383089B2

(12) United States Patent
Rhude

(10) Patent No.: US 11,383,089 B2
(45) Date of Patent: Jul. 12, 2022

(54) METHOD AND DEVICE UTILIZING FAR FIELD SIGNALS TO IDENTIFY AND TREAT UNDER-DETECTED ARRHYTHMIAS

(71) Applicant: PACESETTER, INC., Sytlmar, CA (US)

(72) Inventor: Jennifer Rhude, Carbondale, IL (US)

(73) Assignee: Pacesetter, Inc., Sylmar, CA (US)

( * ) Notice: Subject to any disclaimer, the term of this patent is extended or adjusted under 35 U.S.C. 154(b) by 285 days.

(21) Appl. No.: 15/963,353

(22) Filed: Apr. 26, 2018

(65) Prior Publication Data

US 2019/0329038 A1 Oct. 31, 2019

(51) Int. Cl.
*A61N 1/368* (2006.01)
*A61B 5/00* (2006.01)
(Continued)

(52) U.S. Cl.
CPC .......... *A61N 1/3688* (2013.01); *A61B 5/0006* (2013.01); *A61B 5/0024* (2013.01); *A61B 5/352* (2021.01); *A61B 5/363* (2021.01); *A61B 5/364* (2021.01); *A61N 1/025* (2013.01); *A61N 1/3684* (2013.01); *A61N 1/37223* (2013.01);
(Continued)

(58) Field of Classification Search
CPC .... A61N 1/3688; A61N 1/025; A61N 1/3684; A61N 1/37223; A61N 1/056; A61N 1/0587; A61N 1/36507; A61N 1/36842; A61N 1/36521; A61N 1/39622; A61N 1/3704; A61N 1/362; A61N 1/3222;
(Continued)

(56) References Cited

U.S. PATENT DOCUMENTS 8,914,109 B2 12/2014 Bomzin et al.
9,278,218 B2 3/2016 Karst et al.
(Continued)

OTHER PUBLICATIONS

Wilkoff et al.; "HRS/EHRA/APHRS/SOLAECE Expert Consensus Statement on Optimal Implantable Cardioverter-Defibrillator Programming and Testing" Heart Rhythm Society; 2016; 37 pages.
(Continued)

*Primary Examiner* — Michael W Kahelin
*Assistant Examiner* — Naveed R. Kolia
(74) *Attorney, Agent, or Firm* — The Small Patent Law Group LLC; Dean D. Small

(57) ABSTRACT

Methods, devices and program products are provided for under control of one or more processors within an implantable medical device (IMD). Sensing near field (NF) and far field (FF) signals are between first and second combinations of electrodes coupled to the IMD. The method applies an arrhythmia detection algorithm to the NF signals for identifying events within the NF signal and designates events marker based thereon and monitors the event markers to detect a candidate arrhythmia condition in the NF signals. The candidate under-detected condition comprises at least one of an under-detected arrhythmia or over-sensing. In response to detection of the candidate arrhythmia condition, the method analyzes the FF signals for a presence of an under-detected arrhythmia indicator. The method delivers an arrhythmia therapy based on the presence of the under-detected arrhythmia indicator in the FF signals and the candidate under-detected arrhythmia condition in the NF signals.

24 Claims, 9 Drawing Sheets

(51) Int. Cl.
  *A61N 1/02*     (2006.01)
  *A61N 1/372*    (2006.01)
  *A61B 5/352*    (2021.01)
  *A61B 5/363*    (2021.01)
  *A61B 5/364*    (2021.01)
  *A61N 1/05*     (2006.01)
  *A61N 1/365*    (2006.01)

(52) U.S. Cl.
  CPC ............ *A61N 1/056* (2013.01); *A61N 1/0587* (2013.01); *A61N 1/36507* (2013.01)

(58) Field of Classification Search
  CPC ... A61B 5/0006; A61B 5/0024; A61B 5/0456; A61B 5/0464; A61B 5/0468
  See application file for complete search history.

(56) References Cited

U.S. PATENT DOCUMENTS

| | | |
|---|---|---|
| 9,427,594 B1 | 8/2016 | Bomzin et al. |
| 2011/0125206 A1* | 5/2011 | Bornzin ............... A61B 5/0031 607/5 |
| 2013/0079654 A1* | 3/2013 | Patel ...................... A61B 5/361 600/518 |

OTHER PUBLICATIONS

Thogersen et al.; "Failure to Treat Life-Threatening Ventricular Tachyarrhythmias in Contemporary Implantable Cardioverter-Defibrillators" Circulation: Arrhythmia and Electrophysiology; Sep. 2017; 41 pages.

* cited by examiner

METHOD AND DEVICE UTILIZING FAR FIELD SIGNALS TO IDENTIFY AND TREAT UNDER-DETECTED ARRHYTHMIAS

BACKGROUND

Embodiments of the present disclosure generally relate to methods and devices for detecting potential under detection of ventricular arrhythmias and initiating appropriate treatment.

Implantable medical devices (IMD) provide various types of electrical stimulation, such as in connection with delivering pacing therapy to one or more select chambers of the heart. An IMD may provide both unipolar and bipolar pacing and/or sensing configurations. In the unipolar configuration, the pacing pulses are applied (or responses are sensed) between an electrode carried by the lead and a case of the pulse generator or a coil electrode of another lead within the heart. In the bipolar configuration, the pacing pulses are applied (or responses are sensed) between a pair of electrodes carried by the same lead. IMDs may implement single-chamber, dual-chamber, or triple-chamber functionality. Recently, IMDs have been introduced that stimulate multiple sites in the same chamber, termed multisite stimulation systems or multi-point pacing systems.

IMDs implement various types of arrhythmia detection algorithms to detect different arrhythmia conditions and apply corresponding types of therapy. In general, arrhythmia detection algorithms monitor cardiac signals and label or mark each event with an event type, such as sinus/normal event, slow/bradycardia event, fibrillation event, tachycardia event and the like.

It is desirable to reduce inappropriate therapies. In connection therewith, clinicians are programming faster rate thresholds and longer detection times in connection with detection and treatment of ventricular tachycardia and ventricular fibrillation (VT/VF). The rate thresholds define a beat to beat rate that must be satisfied before the arrhythmia detection algorithm classifies a particular event as VT or VF. Programming longer detection times causes arrhythmia detection algorithms to require multiple events to be classified as a particular arrhythmia event type before the algorithm declares the patient to be experiencing the corresponding arrhythmia episode. For example, the arrhythmia detection algorithm may require a series of 30, 40 or more beats to include a large number of events that are classified with one arrhythmia event type before declaring the arrhythmia and delivering therapy. As another example, the arrhythmia detection algorithm may require a large number of events, with a set period of time, to be classified with the arrhythmia event type before declaring the arrhythmia and delivering therapy.

While programming faster rate thresholds and longer detection times has reduced inappropriate therapies, there is also a potential where such programming parameters have led to therapy being omitted or delayed unnecessarily. In some instances, the arrhythmia detection algorithms are not able to classify a cardiac signal as a particular type of event and instead "trash" or discard the event/beat. Trashed beats are assigned an indeterminate event marker such as a dash ("-"). In other instances, the arrhythmia detection algorithms may classify one or more beats as "sinus" or normal within a series of beats that are classified as fibrillation, tachy or trashed events, thereby creating a irregular marker pattern over a series of event markers. Heretofore, when arrhythmia detection algorithms experience irregular event marker patterns, the irregular event marker patterns may never satisfy detection criteria for the arrhythmia detection algorithm to declare an arrhythmia episode. Hence, the arrhythmia detection algorithm may enter a state where the algorithm waits (for an extended period of time) for the event marker pattern to satisfy the arrhythmia criteria, even though a patient is experiencing an arrhythmia.

SUMMARY

In accordance with embodiments herein, a method is provided. The method is under control of one or more processors within an implantable medical device (IMD). Sensing near field (NF) and far field (FF) signals are between first and second combinations of electrodes coupled to the IMD. The method applies an arrhythmia detection algorithm to the NF signals for identifying events within the NF signal and designates events marker based thereon and monitors the event markers to detect a candidate the under-detected arrhythmia indicator arrhythmia condition in the NF signals. The candidate arrhythmia condition comprises at least one of an under-detected arrhythmia or over-sensing. In response to detection of the candidate arrhythmia condition, the method analyzes the FF signals for a presence of an under-detected arrhythmia indicator. The method delivers an arrhythmia therapy based on the presence of the under-detected arrhythmia indicator in the FF signals and the candidate under-detected arrhythmia condition in the NF signals.

Optionally, the method adjusts the one or more parameters, such as one or more therapy and/or sensing parameters.

Optionally, the method may further comprise setting the under-detected arrhythmia Indicator positive based on a level of cardiac activity. The under-detected arrhythmia indicator may indicate that the FF signal lacks the level of cardiac activity to satisfy a threshold. The method may further comprise setting the under-detected arrhythmia indicator positive when at least one of i) an amount of time for which the FF signal does not include cardiac activity, ii) a number of cardiac cycles for which the FF signal does not include cardiac activity, or, iii) the NF signal is not characteristic of sinus cardiac activity. The monitoring operation may comprise searching for event marker patterns exhibited over a series of event markers, where the event marker patterns are indicative of different types of the candidate conditions. The event marker patterns may comprise a first event marker pattern indicative of an under-detected arrhythmia, and a second event marker pattern indicative of over-sensing. The monitoring may comprise incrementing and decrementing a counter based on the event markers that label different cardiac events within the NF signals.

Optionally, the monitoring and analyzing operations may be performed in connection with NF signals that the arrhythmia detection algorithm declared to not exhibit an arrhythmia episode. The monitoring may further comprise determining whether event markers exhibit a first event marker pattern indicative of an arrhythmia and determining whether event markers exhibit a second event marker pattern indicative of over-sensing. The method may further comprise determining whether an instability criterion is satisfied by the NF signals. The instability criteria may define an unstable condition in which the NF signal (and event markers) is not classified, by the arrhythmia detection algorithm, as a sinus episode or arrhythmia episode, for a predetermined number of cardiac cycles and/or period of time. The instability criteria may represent at least one of i) a condition in which a predetermined number of cardiac cycles have occurred without reaching a detection criteria or ii) a condition in which a predetermined time period has passed without reaching a detection criteria. The arrhythmia detection algorithm may classify cardiac events within the NF signal with the event markers, the event markers comprising at least one of a VF, VT, sinus or indeterminate event markers.

Optionally, the method may further comprise starting a timer in response to an end condition declared for the candidate arrhythmia condition, identifying when a second candidate arrhythmia condition is declared before the timer expires, and based on the identifying, performing the analyzing the FF signals for the presence of an under-detected arrhythmia indicator.

In accordance with embodiments herein, a system is provided. The system comprises an implantable medical device (IMD) coupled to a lead. The lead has electrodes to sense near field (NF) and far field (FF) signals between first and second combinations of electrodes. The system has memory to store the NF and FF signals and to store program instructions. A processor is provided that, when executing the program instructions, is configured to: apply an arrhythmia detection algorithm to the NF signals for identifying events within the NF signal and designate events marker based thereon and monitor the event markers to detect a candidate non-sustained (NS) condition in the NF signals, the candidate under-detected condition comprising at least one of an under-detected arrhythmia or over-sensing. In response to detection of the candidate non-sustained (NS) condition, the processor analyzes the FF signals for a presence of an arrhythmia indicator and delivers an arrhythmia therapy based on the presence of the under-detected arrhythmia indicator in the FF signals and the candidate under-detected condition in the NF signals.

Optionally, the processor may be further configured to set the under-detected arrhythmia indicator positive based on a level and/or type of cardiac activity. The under-detected arrhythmia indicator may indicate that the FF signal lacks the level of cardiac activity to satisfy a threshold. The processor may be further configured to set the under-detected arrhythmia indicator positive when at least one of i) an amount of time for which the FF signal does not include cardiac activity or ii) a number of cardiac cycles for which the FF signal does not include cardiac activity, or iii) the FF signal is not characteristic of sinus cardiac activity. The event marker patterns may comprise a first event marker pattern indicative of an under-detected arrhythmia, and a second event marker pattern indicative of over-sensing. The processor may be further configured to perform the monitor and analyze operations in connection with NF signals that the arrhythmia detection algorithm declared to not exhibit an arrhythmia episode.

Optionally, the processor may be further configured to determine whether event markers exhibit a first event marker pattern indicative of a non-sustained arrhythmia and determine whether event markers exhibit a second event marker pattern indicative of non-sustained over-sensing. The processor and memory may be housed within the IMD. An external device may house the processor and housing. The processor may be further configured to determine whether an arrhythmia testing timer has expired. The arrhythmia testing timer may represent a predetermined maximum period of time to elapse since the arrhythmia detection algorithm began attempting to identify an arrhythmia.

DETAILED DESCRIPTION

Figure 1:
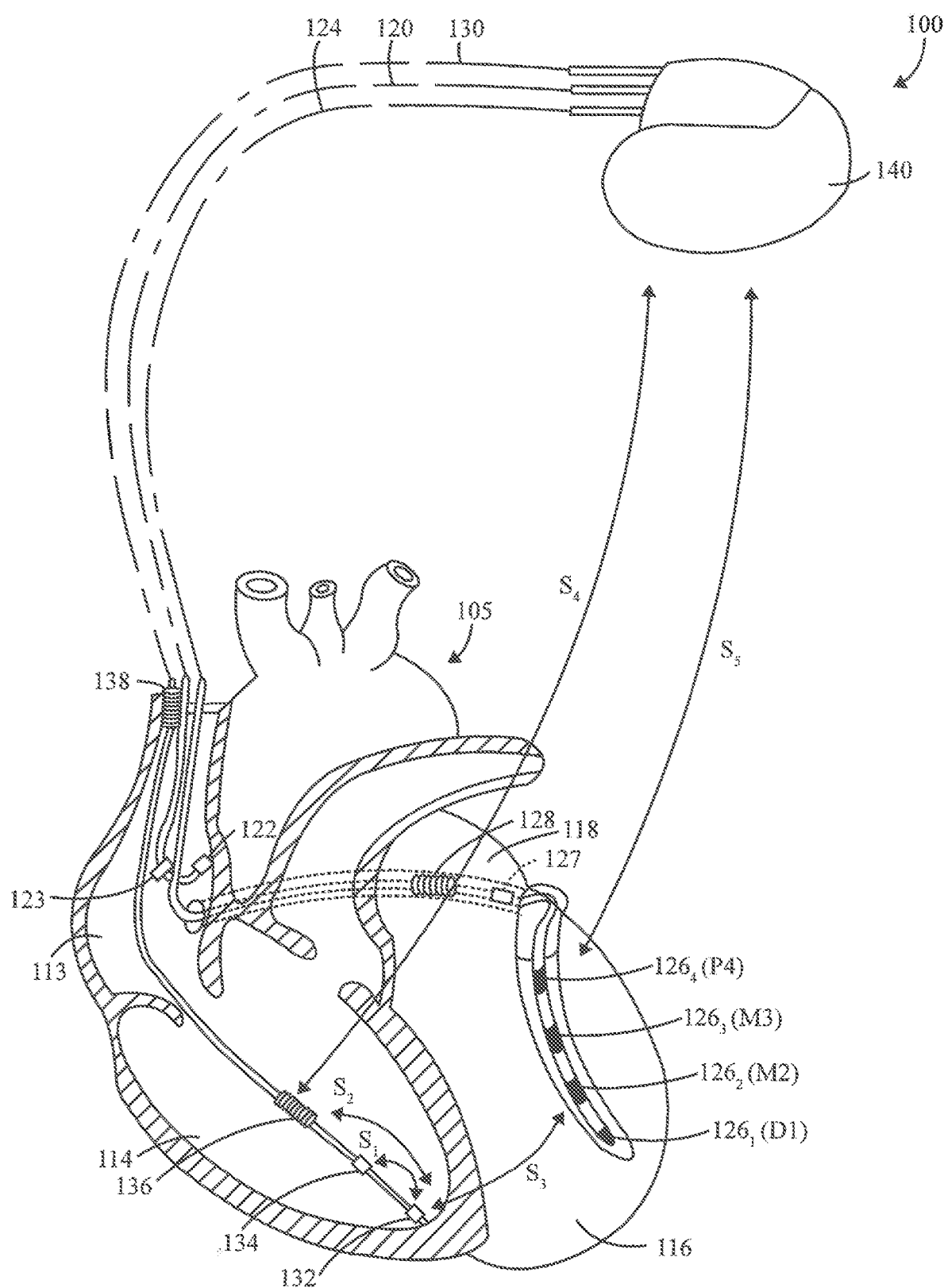
FIG. 1 illustrates an IMD coupled to a heart in a patient and implemented in accordance with one embodiment herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

The term "over-sensing", as used throughout, refers to an operation by an IMD that occurs when electrical signals are inappropriately recognized, by an IMD, as native cardiac activity and pacing/ATP/shocking is inhibited. The inappropriate signals may be large P or T waves, skeletal muscle activity or lead contact problems.

The term "under-sensing", as used throughout, refers to an operation by an IMD occurs when the IMD fails to recognize spontaneous myocardial depolarization (e.g., physiologic cardiac activity).

The term "under-detected", as used throughout, refers to a condition in which an IMD does not classify an arrhythmia episode accurately due to misidentification of one or more beats within the arrhythmia episode.

In accordance with embodiments herein, methods and systems are described that analyze far field (FF) signals for arrhythmia indicators in connection with recognizing and differentiating between an ongoing under-detected arrhythmia, and/or over-sensing episode. Embodiments herein accelerate a final determination of an arrhythmia and the corresponding therapy in connection with preventing an ongoing non-sustained condition from continuing untreated for an excessive period of time. Embodiments herein utilize characteristics of interest from the FF signal to detect and label an arrhythmia as under-detected by a pre-existing arrhythmia detection algorithm and to increase a likelihood of therapy delivery during the ongoing condition either by I) adjusting detection parameters, II) adjusting therapy parameters and/or III) forcing an arrhythmia declaration and therapy.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 titled "Neurostimulation Method and System to Treat Apnea" and U.S. Pat. No. 9,044,610 titled "System And Methods For Providing A Distributed Virtual Stimulation Cathode For Use With An Implantable Neurostimulation System," which are hereby incorporated by reference. Additionally, or alternatively, the IMD may include one or more structural and/or functional aspects of the device(s) described in U.S. Pat. No. 9,216,285 titled "Leadless Implantable Medical Device Having Removable and Fixed Components" and U.S. Pat. No. 8,831,747 titled "Leadless Neurostimulation Device And Method Including The Same", which are hereby incorporated by reference. Additionally, or alternatively, the IMD may include one or more structural and/or functional aspects of the device(s) described in U.S. Pat. No. 8,391,980 titled "Method and System for Identifying a Potential Lead Failure in an Implantable Medical Device" and U.S. Pat. No. 9,232,485 titled "System And Method For Selectively Communicating With An Implantable Medical Device," which are hereby incorporated by reference.

FIG. 1 illustrates an IMD 100 coupled to a heart in a patient and Implemented in accordance with one embodiment. The IMD may communicate with an external device such as a programmer, an external defibrillator, a workstation, a portable computer, a personal digital assistant, a cell phone, a bedside monitor and the like. The IMD may represent a cardiac monitoring device, pacemaker, cardioverter, cardiac rhythm management device, defibrillator, neurostimulator, leadless monitoring device, leadless pacemaker and the like, implemented in accordance with one embodiment of the present invention. The IMD 100 may be a single-chamber or dual-chamber stimulation device capable of treating both fast and slow arrhythmias with stimulation therapy, including cardioversion, defibrillation, and pacing stimulation, including CRT. Optionally, the IMD 100 may be configured for multi-site left ventricular (MSLV) pacing, which provides pacing pulses at more than one site within the LV chamber each pacing cycle. To provide atrial chamber pacing stimulation and sensing, IMD 100 is shown in electrical communication with a heart 105 by way of a right atrial (RA) lead 120 having an atrial tip electrode 122 and an atrial ring electrode 123 implanted in the atrial appendage 113. A right ventricular (RV) lead 130 has a ventricular tip electrode 132, an RV ring electrode 134, an RV coil electrode 136, and a superior vena cava (SVC) coil electrode 138. The RV lead 130 is transvenously inserted into the heart 105 so as to place the RV coil electrode 136 in the RV apex, and the SVC coil electrode 138 in the superior vena cava.

To sense left atrial and ventricular cardiac signals and to provide left ventricle 116 (e.g., left chamber) pacing therapy, IMD 100 is coupled to a multi-pole LV lead 124 designed for placement in the "CS region." As used herein, the phrase "CS region" refers to the venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus. In an embodiment, an LV lead 124 is designed to receive atrial and ventricular cardiac signals and to deliver left ventricular pacing therapy using a set of multiple LV electrodes 126 that includes electrodes 1261, 1262, 1263, and 1264 (thereby providing a multipolar or multi-pole lead). The LV lead 124 also may deliver left atrial pacing therapy using at least an LA ring electrode 127 and shocking therapy using at least an LA coil electrode 128. In alternate embodiments, the LV lead 124 includes the LV electrodes 1261, 1262, 1263, and 1264, but does not include the LA electrodes 127 and 128. Although three leads 120, 124, and 130 are shown in FIG. 1, fewer or additional leads with various numbers of pacing, sensing, and/or shocking electrodes may optionally be used. The LV electrodes 1261, 1262, 1263, and 1264 may be referred to respectively as electrodes D1, M2, M3, and P4 (where "D" stands for "distal", "M" stands for "middle", and "P" stands from "proximal", and the numbers are arranged from most distal to most proximal, as shown in FIG. 1). Optionally, more or fewer LV electrodes may be provided on the lead 124 than the four LV electrodes D1, M2, M3, and P4.

While FIG. 1 illustrates multiple leads provided within the heart, it is understood that only one or more of the leads 124, 120 and 130 may be utilized and the other leads 124, 120 and 130 may be removed. For example, the lead 120 and the lead 124 may be removed, leaving only the lead 130 to support right side ventricular pacing and sensing.

In a pacing vector or a sensing vector, each LV electrode 126 may be controlled to function as a cathode (negative electrode). Pacing pulses may be directionally provided between electrodes to define a pacing vector. Optionally, combinations of LV electrodes 126 are paired with one another to operate as a common virtual electrode, such as a common virtual cathode, when delivering pacing therapies. The electrodes that define the pacing vectors may be electrodes in the heart 105 or located externally to the heart 105 (e.g., on a housing/case device 140). For example, the housing/case 140 may be referred to as the CAN 140 and function as an anode in unipolar pacing and/or sensing vectors. The LV electrodes 126 may be used to provide various different vectors. Some of the vectors are intraventricular LV vectors (e.g., vectors between two of the LV electrodes 126), while other vectors are interventricular vectors (e.g., vectors between an LV electrode 126 and the RV coil 136 or another electrode remote from the left ventricle 116).

As explained herein, embodiments utilize near field (NF) and far field (FF) sensing vectors to collect near field and far field signals for use herein. FIG. 1 illustrates examples of different sensing vectors between different combinations of electrodes. The sensing vectors are divided into near field sensing vectors S1-S3 and far field sensing vectors S4-S5. The near field sensing vectors S1-S3 sense near field signals, while the far field sensing vectors sense far field signals. For example, NF sensing vector S1 is between tip and ring electrodes 132, 134, NF sensing vector S2 is between tip and coil electrodes 132, 136 and NF sensing vector S3 is between RV tip electrode 132 and one or more LV electrodes 126. The FF sensing vector S4 is between the RV coil electrode 136 and the CAN electrode formed by the housing 140 of the IMD. Additionally, or alternatively, the FF sensing vector S5 may be utilized between the RV tip electrode 132 and the CAN electrode formed by the housing 140 of the IMD.

Optionally, the sensing vectors S1, S2 and S4 may be provided in a configuration in which the RV lead 130 is utilized alone, while the leads 120, 124 are omitted entirely. Additionally, or alternatively, NF sensing vector S3 and FF sensing vector S5 may be utilized in a configuration with RV lead 130 and LV lead 124, with or without the inclusion of the RA lead 120. Below is a list of example bipolar sensing vectors with LV cathodes that may be used for sensing using the LV electrodes D1, M2, M3, and P4 and the. In the following list, the electrode to the left of the arrow is the cathode, and the electrode to the right of the arrow is the anode: D1→M2; D1→P4; M2→P4; M3→M2; M3→P4; and P4→M2.

Figure 2A:
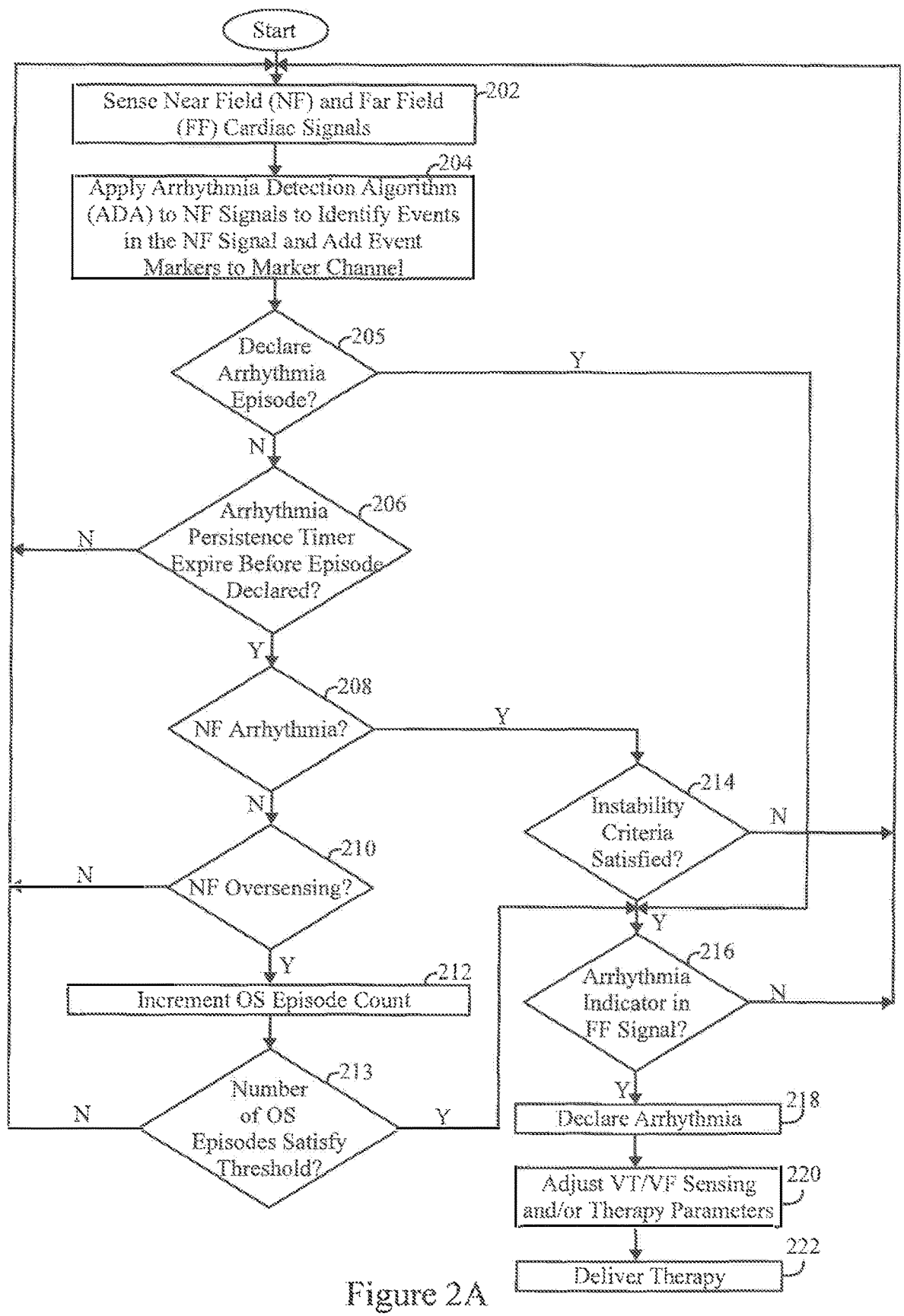
FIG. 2A illustrates a process for utilizing far field signals to discriminate between arrhythmias and non-sustained conditions in accordance with embodiments herein.

FIG. 2A illustrates a process for utilizing far field signals to discriminate between arrhythmias and non-sustained conditions in accordance with embodiments herein. Under control of one or more processors within an IMD, at 202, sensors sense near field (NF) and far field (FF) signals between first and second combinations of electrodes coupled to the IMD and/or to an external device. By way of example, an IMD may sense NF and FF signals and internally and automatically implement the operations of FIG. 2A, including delivery of an arrhythmia therapy. Additionally, or alternatively, the IMD may sense the NF and FF signals, wirelessly convey the NF and FF signals in real time to an external device, where the external device performs all or a portion of the operations of FIG. 2A discussed herein. The external device discriminates between arrhythmias, oversensing conditions and the like, and based thereon, the external device directs the IMD to deliver the appropriate therapy and adjust sensing and/or therapy parameters.

In accordance with embodiments herein, the NF and FF signals are sensed at the same time or contemporaneous with one another, such that the NF and FF signals are indicative of a common series of cardiac events/beats. Additionally, or alternatively, the NF and FF signals may be sensed at different points in time. For example, the NF signals may be sensed during a first period of time for analysis and monitoring in connection with the operations described below at 204-214. In the event that the process of FIG. 2A reaches the operation at 216, FF signals may then be sensed over a desired number of cardiac events/beats during a second period of time (subsequent to the first period of time) for analysis at 216.

At 204, the one or more processors apply an arrhythmia detection algorithm to the NF signals to identify events within the NF signal and designate event markers based thereon. The processors classify or label the cardiac events/beats with event markers. The processors perform the classification/labeling over a predetermined number of cardiac events/beats to form a series of events marker. When the arrhythmia detection algorithm identifies a potential beginning of an arrhythmia, the arrhythmia detection algorithm starts a timer. The timer represents an arrhythmia testing timer which corresponds to a predetermined maximum period of time that the arrhythmia detection algorithm is allowed to test for and identify an arrhythmia. For example, once the arrhythmia detection algorithm identifies a potential start of an arrhythmia, the algorithm continues to monitor NF signals for a series of cardiac events. The processors search for a sufficient number of cardiac events that have a particular arrhythmia characteristic. In response thereto, the arrhythmia detection algorithm declares an arrhythmia episode. For example, when a start of a potential ventricular tachycardia episode is identified, the arrhythmia detection algorithm may bin/count cardiac events having a sufficiently narrow RR interval to qualify as tachycardia events. When a predetermined number of tachycardia cardiac events (e.g., 24 VT events) are counted successively or within a predetermined period of time, the arrhythmia detection algorithm declares a tachycardia episode. A similar process may be performed in connection with ventricular fibrillation events, but with a different predetermined number of binned/counted events required before declaring a fibrillation episode (e.g., 16 VF events). While FIG. 2A illustrates logical flow progressing from 204 to 206, it is recognized that in at least some implementations, the operations at 202, 204 for sensing NF signals, classifying cardiac events and adding event markers may be continuously performed in parallel and independent of the remaining operations of FIG. 2A at 206-222.

At 205, the one or more processors analyze the event markers and determine whether to declare an arrhythmia episode. For example, the processors may search for a first number X of arrhythmia event markers out of a second number Y of total cardiac events (e.g., 30 VT/VF events out of 40 total events). As another example, the processors may search for a first number X of arrhythmia event markers within a predetermined period of time (e.g., 90 VT/VF events within a 2 minute period of time). When an arrhythmia episode is declared at 205, the processors reset the arrhythmia testing timer and flow branches to 216. Alternatively, when an arrhythmia episode is not declared at 205, flow continues to 206. Optionally, the arrhythmia detection algorithm implemented at 204 and 205 may be performed independent of and in parallel with the operations of FIG. 2. The operations at 206-216 are performed in connection with NF signals that the arrhythmia detection algorithm declared to not exhibit an arrhythmia episode at 205.

At 206, the one or more processors determine whether the arrhythmia testing timer has expired. When the arrhythmia testing timer expires, the processors determine that the predetermined maximum period of time has elapsed since the arrhythmia detection algorithm began attempting to identify a present arrhythmia. In connection therewith, the processors monitor the series of event markers to search for a candidate arrhythmia condition in the NF signals. The candidate under-detected arrhythmia condition may represent different types of conditions, such as, but not limited to, at least one of an under-detected arrhythmia or over-sensing. The processors may search for certain event marker patterns exhibited over the series of event markers, where different event marker patterns are indicative of different types of conditions. For example, one or more event marker patterns may be indicative of an under-detected arrhythmia, while one or more other event marker patterns may be indicative of over-sensing.

The event marker patterns may be defined in various manners. For example, the event marker pattern may be implemented utilizing one or more counters that count the number of events having an event marker of interest. For example, a VF counter may be incremented for each cardiac event labeled with a VF event marker. Optionally, the VF counter may be decremented for each cardiac event that is not labeled with a VF event marker. For example, a VT counter may be incremented for each cardiac event labeled with a VT event marker. Optionally, the VT counter may be decremented for each cardiac event that is not labeled with a VT event marker. Optionally, a VF/VT counter may be used to count both VT and VF events. Optionally a timer may be utilized where as long as a certain number of events met a criteria the condition would still be classified as ongoing. As noted herein, in some instances, cardiac events may be labeled as sinus or indeterminate. As another example, when a cardiac event with a sinus event marker (or predetermined number of successive cardiac events with successive sinus event markers) occurs, the VF and/or VT counter(s) may be reset and the condition is declared to be over. As another example, when an indeterminate event marker occurs, the VT and/or VF counter(s) may be maintained unchanged and/or decremented.

Additionally, or alternatively, the processors may utilize one or more predetermined event marker patterns that correspond to a predetermined number of events with a particular event marker occurring within a predetermined total number of events and/or over a predetermined period of time. For example, the predetermined event marker pattern may represent a set of 6 or more cardiac events that include two or more indeterminate event markers. As another example, the predetermined event marker pattern may represent a set of 10 or more cardiac events that include two or more different types of event markers (e.g., 3 sinus event markers, 4 VF event markers and 3 indeterminate event markers).

The processors, when monitoring the series of event markers, may not identify any candidate arrhythmia condition in the NF signals. When the processors do not identify a candidate arrhythmia condition, flow returns to 202, where sensing continues for additional NF signals (and optionally FF signals). When a candidate arrhythmia condition is identified at 206, flow moves to 208.

Figure 2B:
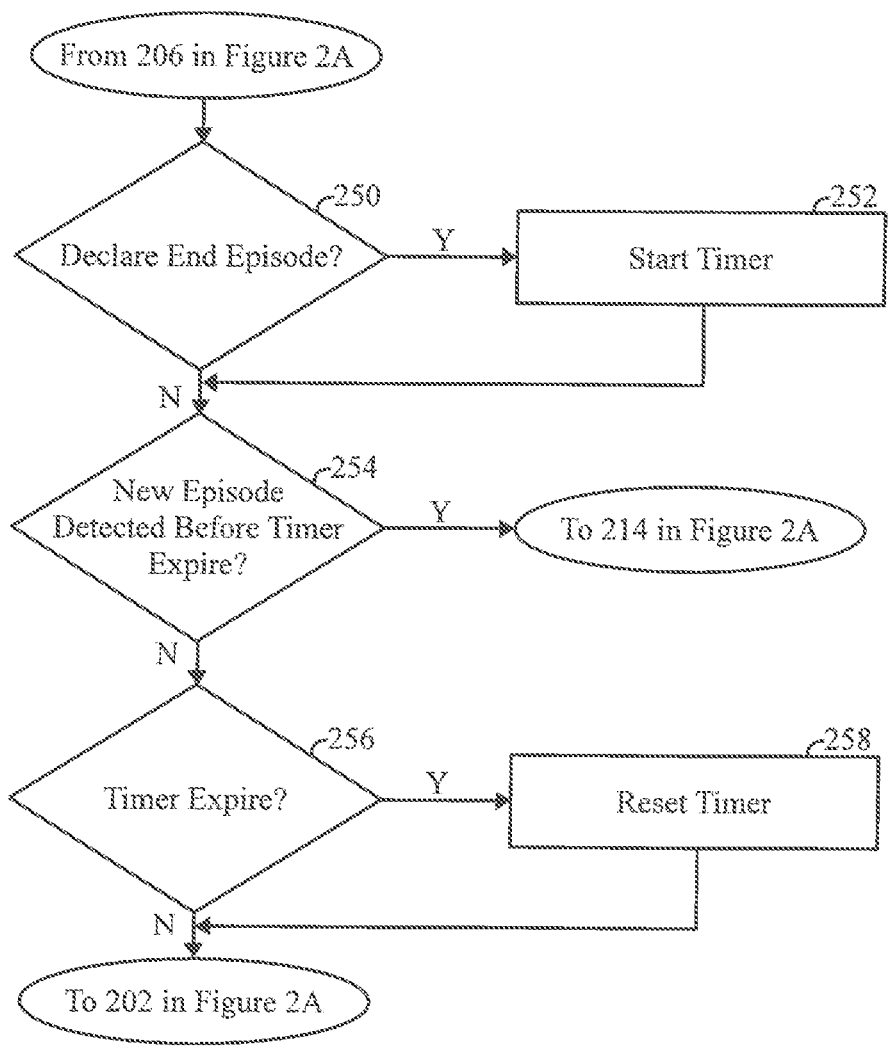
FIG. 2B illustrates a process for tracking occurrence of new arrhythmia episodes within a redetection time period of one another in accordance with embodiments herein.

Optionally, flow may move in parallel to FIG. 2B. As explained hereafter in connection with the operations of FIG. 2B, the one or more processors utilize a redetection timer to determine whether a new arrhythmia episode is detected within a predetermined time interval after a prior episode is declared to end. When a new episode occurs within the redetection time interval, flow returns from FIG. 2B to 214 where the instability criteria are analyzed as described hereafter.

At 208 and 210, the one or more processors identify the type of candidate arrhythmia condition, such as an under-detected arrhythmia and/or over-sensing.

At 208, the one or more processors determine whether the series of event markers exhibit an event marker pattern indicative of an arrhythmia. When the series of event markers do not correspond to an event marker pattern indicative of an arrhythmia, flow moves to 210. Alternatively, when an arrhythmia is indicated at 208, flow moves to 214.

At 214, the one or more processors determine whether an instability criterion is satisfied. The instability criteria defines an unstable condition in which the NF signal (and event markers) is not classified, by the arrhythmia detection algorithm, as a sinus episode, nor arrhythmia episode, for a predetermined number of cardiac cycles and/or period of time. For example, the processors may determine that 10 seconds, 15 seconds, etc. have passed and no events have been labeled with event markers. As another example, the instability criteria may represent a condition in which a predetermined number of cardiac cycles have occurred without reaching a detection criteria (at 205). Additionally, or alternatively, the instability criteria may represent a condition in which a predetermined time period has passed without reaching a detection criteria. When the instability criteria is not satisfied, the flow returns to the beginning of the operations of FIG. 2. When the instability criteria is satisfied, flow moves to 216.

At 216, the one or more processors analyze the far field signals for a presence of an under-detected arrhythmia indicator. In accordance with at least one embodiment, the under-detected arrhythmia indicator may represent an indication as to whether the FF signal includes or lacks valid cardiac activity. The processors may determine a presence or absence of valid cardiac activity based on whether a level of cardiac activity (e.g., number of peaks, slope changes, total energy) satisfies a threshold (e.g., peak count threshold, slope change threshold count, total energy threshold). When the FF signal does not include any or sufficient cardiac activity, the under-detected arrhythmia indicator is set positive. When the FF signal does include any or sufficient valid cardiac activity, the under-detected arrhythmia indicator is set negative. Optionally, when the FF signal includes at least some evidence of cardiac activity, the processors may not adjust the VT/VF sensing and/or therapy parameters.

For example, the under-detected arrhythmia indicator may represent an amount of time X or number of cardiac cycles Y, for which the FF signal does not include/sense cardiac activity. The processors may compare an amplitude of the FF signal to a discrimination threshold, wherein only portions of the FF signal that exceed the discrimination threshold are considered to represent valid cardiac activity. Portions of the FF signal below the discrimination threshold may be classified as noise or other non-physiologic information. At 216, the one or more processors may analyze the signal content of the FF signal that exceeds the discrimination threshold in various manners. For example, the processors may simply count a number of peaks in the FF signal that exceed the discrimination threshold. The processors may determine that the FF signal includes valid cardiac activity when a sufficient number of peaks are identified. The processors determine that the FF signals do not include valid cardiac activity when too few peaks are identified.

Additionally, or alternatively, the processors may apply various physiologic morphology templates or criteria to the FF signals. The physiologic morphology templates may be correlated with the entire FF signal and/or only the portion of the FF signal that exceed the discrimination threshold. The processors may determine that the FF signal Includes valid cardiac activity when a morphology of the FF signal sufficiently correlates to a physiologic morphology template. The processors determined that the FF signal does not include valid cardiac activity when the morphology of the FF signal does not correlate to a physiologic morphology template. Additional or alternative characteristics of the FF signal may be analyzed to identify a presence or absence of valid cardiac activity. When the far field signals do not include an under-detected arrhythmia Indicator, flow returns to the beginning of the operations of FIG. 2. Otherwise, when an under-detected arrhythmia indicator is identified at 216, flow moves to 218.

In the foregoing example, it is contemplated that the FF signals are sensed at 202 contemporaneous with sensing NF signals. Optionally, far field signals may be sensed at 216 for a predetermined period of time and then analyzed for the presence of the under-detected arrhythmia Indicator.

At 218, the one or more processors declare the near field and far field signals to exhibit an arrhythmia condition. The processors identify the type of arrhythmia and a corresponding therapy based on the under-detected arrhythmia indicator in the far field signals and based on the event marker pattern corresponding to the near field signals.

At 220, the one or more processors adjust one or more sensing parameters, such as one or more VT/VF sensing parameters, in order to render the VT/VF detection algorithm more sensitive or aggressive. By way of example, the sensing parameters may be adjusted by increasing a detection interval by a predetermined number of milliseconds. As another example, the sensing parameters may be adjusted by combining bins that are used to count events having different detection intervals. Additionally, or alternatively, at 220 the processors may adjust one or more therapy parameters. For example, the processors may adjust a therapy parameter directing the IMD to skip ATP therapy and/or low energy shocks, and instead deliver another type of therapy. The processors may adjust filters and/or sensing parameters.

At 222, the processors deliver the arrhythmia therapy in response to the presence of the under-detected arrhythmia indicator in the FF signals and the candidate under-detected arrhythmia condition in the NF signals. The arrhythmia therapy may be delivered based on the therapy parameter adjustments at 220 or independent thereof.

In accordance with the foregoing process, embodiments herein utilize the fact that far field sensing may become somewhat unreliable during polymorphic VT and polymorphic VF. In connection therewith, the operation at 206 monitors the series of event markers assigned by the arrhythmia detection algorithm. The monitoring operation at 206 detects event marker patterns of interest assigned by the arrhythmia detection module. An event marker pattern of interest may correspond to a series of event markers where successive event markers switch between one or more "binned" events, such as switching between VT or VF events, trashed/indeterminate events and sinus events. When a series of event markers include successive event markers that switch between one or more of VT/VF events, trashed events and sinus events, the event marker pattern represents an indeterminate pattern in that the type of event marker changes between successive events in a manner that is not strongly indicative or characteristic of a physiologic sinus pattern, a physiologic abnormal pattern or a non-physiologic pattern (e.g., a lead failure). When the event marker pattern represents an indeterminate pattern, the processes herein analyze signals from a confirmation channel, namely far field signals collected along a far field sensing vector. At 214 and 216, when the processors determined that the far field signal is indicative of an arrhythmia (e.g., no signal sensed), there is high likelihood that the IMD is experiencing under detection of VF an ongoing basis sufficient to justify delivery of a high-voltage therapy.

Alternatively, the event marker pattern may not be indicative of a candidate arrhythmia. When the processors determine that the series of event markers do indicate some type of candidate indeterminate condition, but not a candidate arrhythmia, flow continues to 210. At 210, the one or more processors determine whether the series of event markers exhibit an event marker pattern indicative of over-sensing. When n over-sensing is indicated at 210, flow moves to 212. Alternatively, when the series of event markers do not correspond to an event marker pattern indicative of over-sensing, flow returns to the beginning of the operations of FIG. 2.

At 212, the one or more processors increment a counter that maintains a running count of a number of candidate over-sensing episodes. For example, the processors may maintain an "X of Y" counter, in which the processors track when X over-sensing (OS) episodes occur in a period of time Y. When the predetermined number of OS episodes occurs within the select period of time, the processors interpret this condition to represent a potential or candidate over-sensing condition that warrants verification by analyzing the far field signals for an under-detected arrhythmia indicator.

At 213, the one or more processors compare the "X of Y" counter to an X of Y threshold to determine whether the number of OS episodes satisfies the corresponding threshold. When the threshold is not satisfied, flow returns to the beginning of FIG. 2. Alternatively, when the threshold is satisfied, the processors interpret the condition to represent a potential or candidate over-sensing condition that warrants verification by analyzing the far field signals for the under-detected arrhythmia indicator. Thus, when the threshold is satisfied, flow moves to 216 where the process continues as described herein.

Next, the operations of FIG. 2A are described in connection with example cardiac signals and event markers.

Figure 3A:
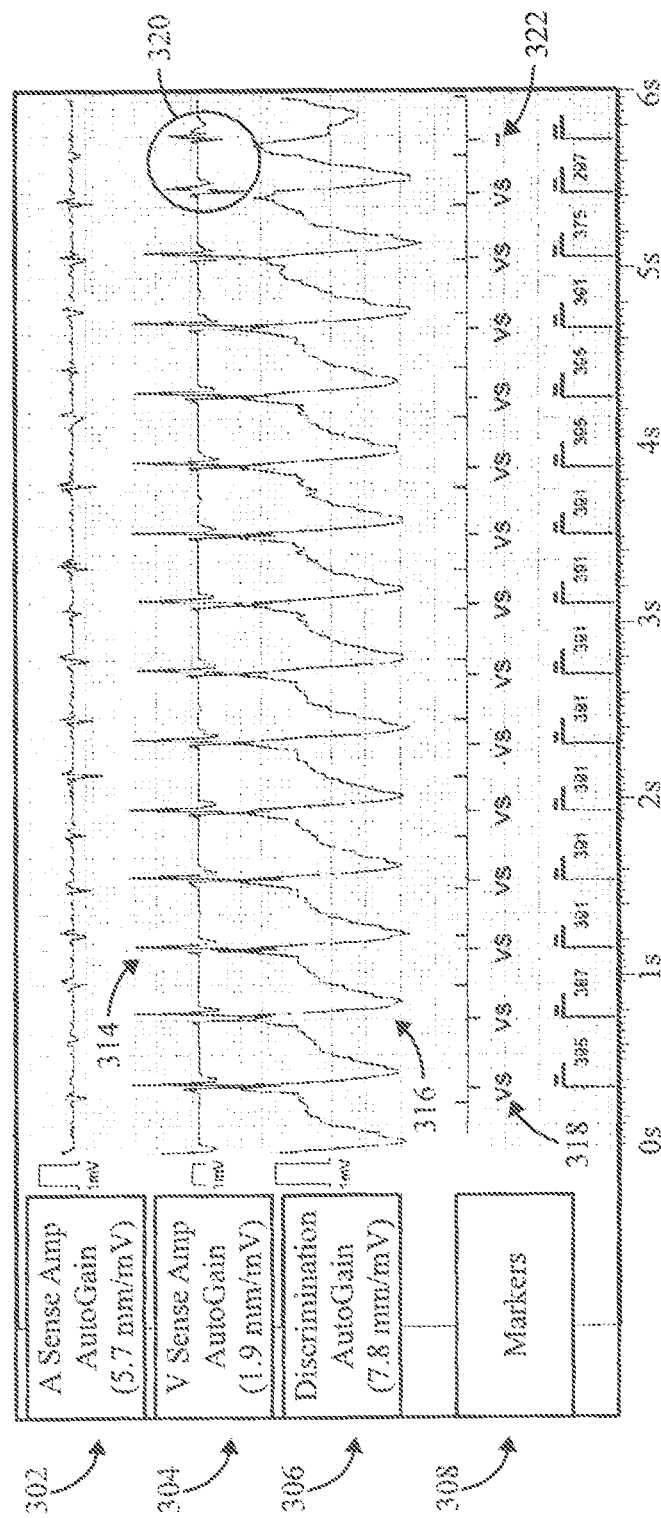
FIG. 3A illustrates panels of electrocardiogram (EGM) cardiac signals sensed over corresponding sensing vectors by an IMD in accordance with embodiments herein.

FIGS. 3A-3D Illustrate panels of electrocardiogram (EGM) cardiac signals sensed over corresponding sensing vectors by an IMD, where each panel corresponds to a strip of cardiac signals of approximately 6-7 seconds in length. With reference to FIG. 3A, the EGM signals include an atrial sensing channel 302, a ventricular sensing channel 304, a far field sensing channel 306 and an event marker channel 308. The atrial sensing channel 302 is not utilized in connection with the above-described embodiments. With reference to FIG. 2, at 202, NF signals 314 are sensed over the ventricular sensing channel 304 between a corresponding first combination of electrodes, while the FF signals 316 are sensed over the sensing channel 306 between a corresponding second combination of electrodes. The arrhythmia detection algorithm analyzes the NF signals 314 to identify events therein and designate event markers 318 in the event marker channel 308. At 206 (FIG. 2), the IMD monitors the event markers 318 to detect candidate arrhythmia conditions in the NF signals 314.

In FIG. 3A, the NF signals 314 exhibit consistent regular cardiac signals that are labeled by the arrhythmia detection algorithm as ventricular sensed (VS) events by event markers 318. Near the end of the EGM panel in FIG. 3A, the NF signals diminish in amplitude and begin occurring faster (at 320, shortly before the 6 second point in the collection of cardiac signals) which results in an indeterminate "–" event marker 322 to be designated in the event marker channel 308.

Figure 3B:
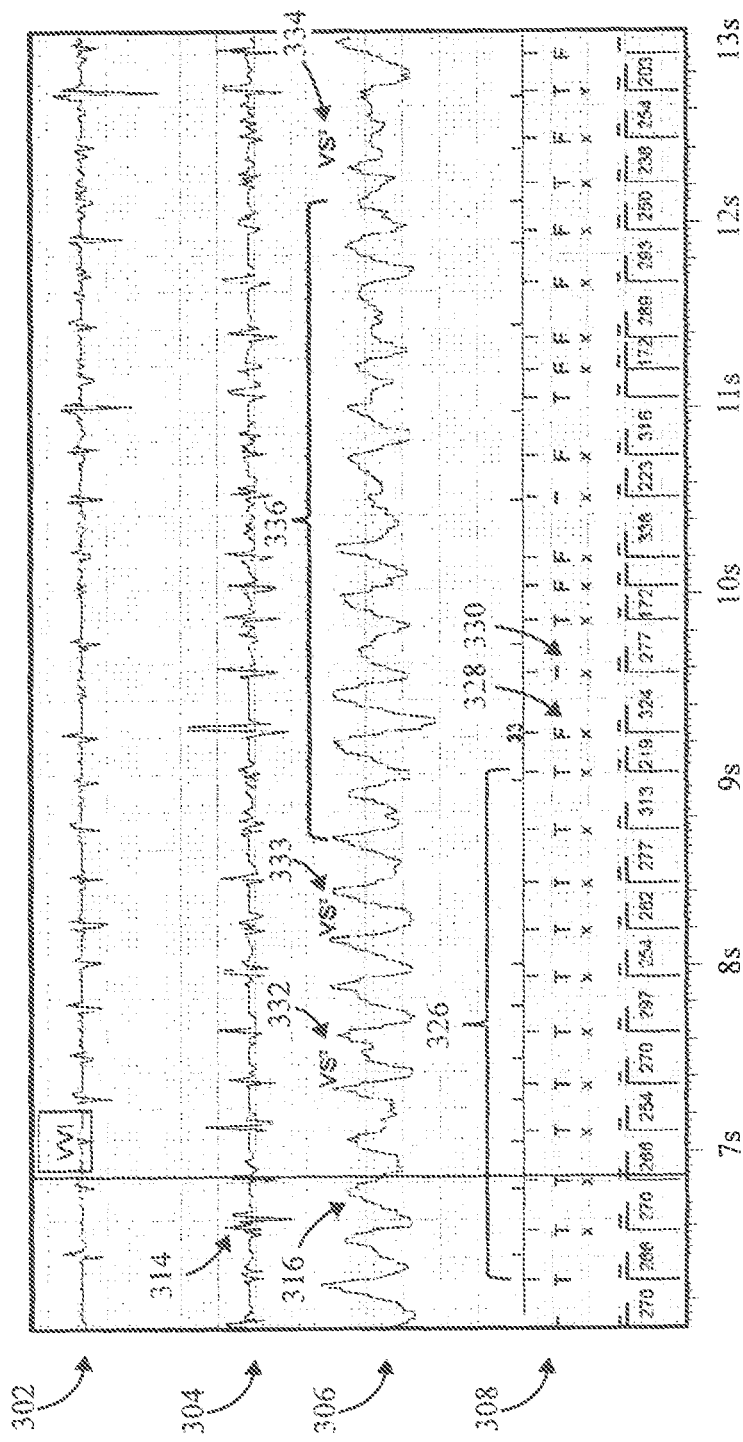
FIG. 3B Illustrates panels of electrocardiogram (EGM) cardiac signals sensed over corresponding sensing vectors by an IMD in accordance with embodiments herein.

In FIG. 3B, the EGM panel extends from 6 seconds to 13 seconds, during which the NF signal 314 becomes sporadic with substantial variations in amplitude and at an Increased rate. The arrhythmia detection algorithm identifies tachycardia (T), fibrillation (F) and indeterminate (–) events from the NF signal 314 and labels the events with a series of T, F and – event markers. For example, tachycardia event markers are identified for a series of events at 326, followed by a fibrillation event marker 328, followed by an indeterminate event marker 330, followed by more tachycardia event markers. Thereafter, an uneven pattern of tachycardia, fibrillation and indeterminate event markers are designated between the 10 second and 13 second points in the EGM panel.

In accordance with embodiments herein, the arrhythmia detection algorithm also analyzes the far field sensing channel 306 for physiologic events and includes event markers in connection there with. FIG. 3B illustrates sensed event markers 332-334 that were identified by the arrhythmia detection algorithm from the far field sensing channel 306. While the far field sensing channel 306 illustrates cardiac activity all along the panel in FIG. 3B, the arrhythmia detection algorithm did not Identify any ventricular sensed events, other than the events identified by sinus event markers 332-334. Instead, the arrhythmia detection algorithm may classify the remaining portion (e.g., within region 336) to represent noise. The arrhythmia detection algorithm may not have identified any other sensed events in the remaining segments of the far field sensing channel 306 due to one or more characteristics of the far field sensing channel 306 (e.g., amplitude and/or shape) falling below a corresponding threshold.

Figure 3C:
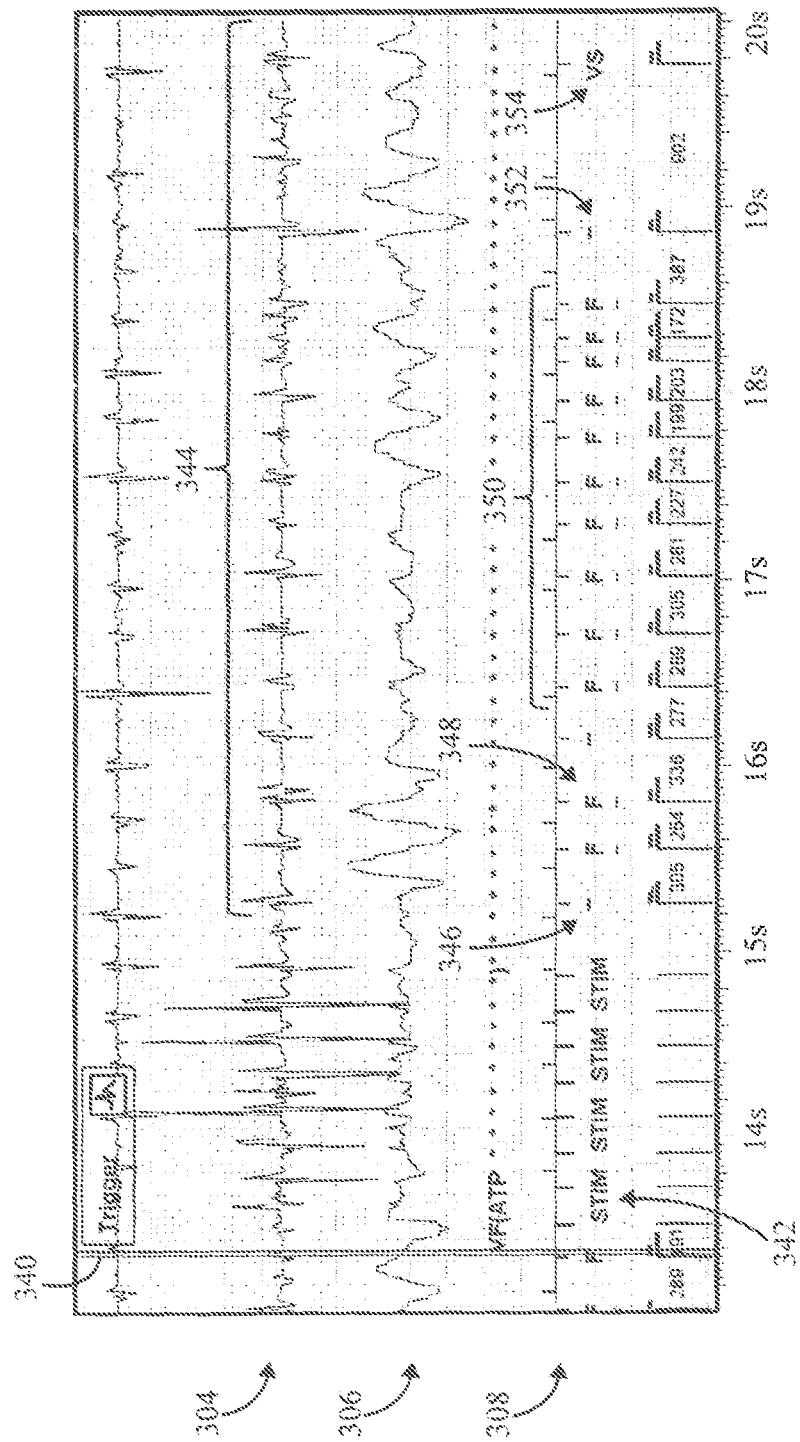
FIG. 3C Illustrates panels of electrocardiogram (EGM) cardiac signals sensed over corresponding sensing vectors by an IMD in accordance with embodiments herein.

In FIG. 3C, the arrhythmia detection algorithm ultimately declares an arrhythmia episode at 340, after which ATP therapy is delivered as noted by the STIM event markers 342. However, the arrhythmia was declared after a relatively long number of cardiac events (also referred to as binned cycles). For example, as shown in the EGM panel of FIG. 3B, 27 binned events are classified as tachycardia, fibrillation or indeterminate events, before declaring the arrhythmia. The total number of binned events, 27, exceeds the selected number of events for the zones for different types of arrhythmia events. For example, an IMD may be programmed to declare a ventricular tachycardia after detecting 24 tachycardia event markers, and to declare a ventricular fibrillation after detecting 12 fibrillation event markers. In the example of FIGS. 3B-3C, neither bin threshold for the tachycardia zone or the fibrillation zone were reached as the event markers in FIG. 3B switched in an uneven manner between three different types of events (tachy, fibrillation and indeterminate).

Returning to FIG. 3C, after the ATP therapy is delivered at STIM event markers 342, the arrhythmia episode is not terminated. Instead, as shown in the segment 344 of the ventricular sensing channel 304, the NF signals continue to modulate in amplitude and frequency in an abnormal manner. Over the segment 344, the arrhythmia detection algorithm declares individual events as indeterminate or fibrillation events, as noted at event markers 346, 348. After a series of fibrillation event markers 350, followed by an indeterminate event marker 352, a sinus event is declared at sinus event marker 354. However, as indicated from the segment 344 in the ventricular sensing channel 304, the patient is not yet experiencing a sinus rhythm.

Figure 3D:
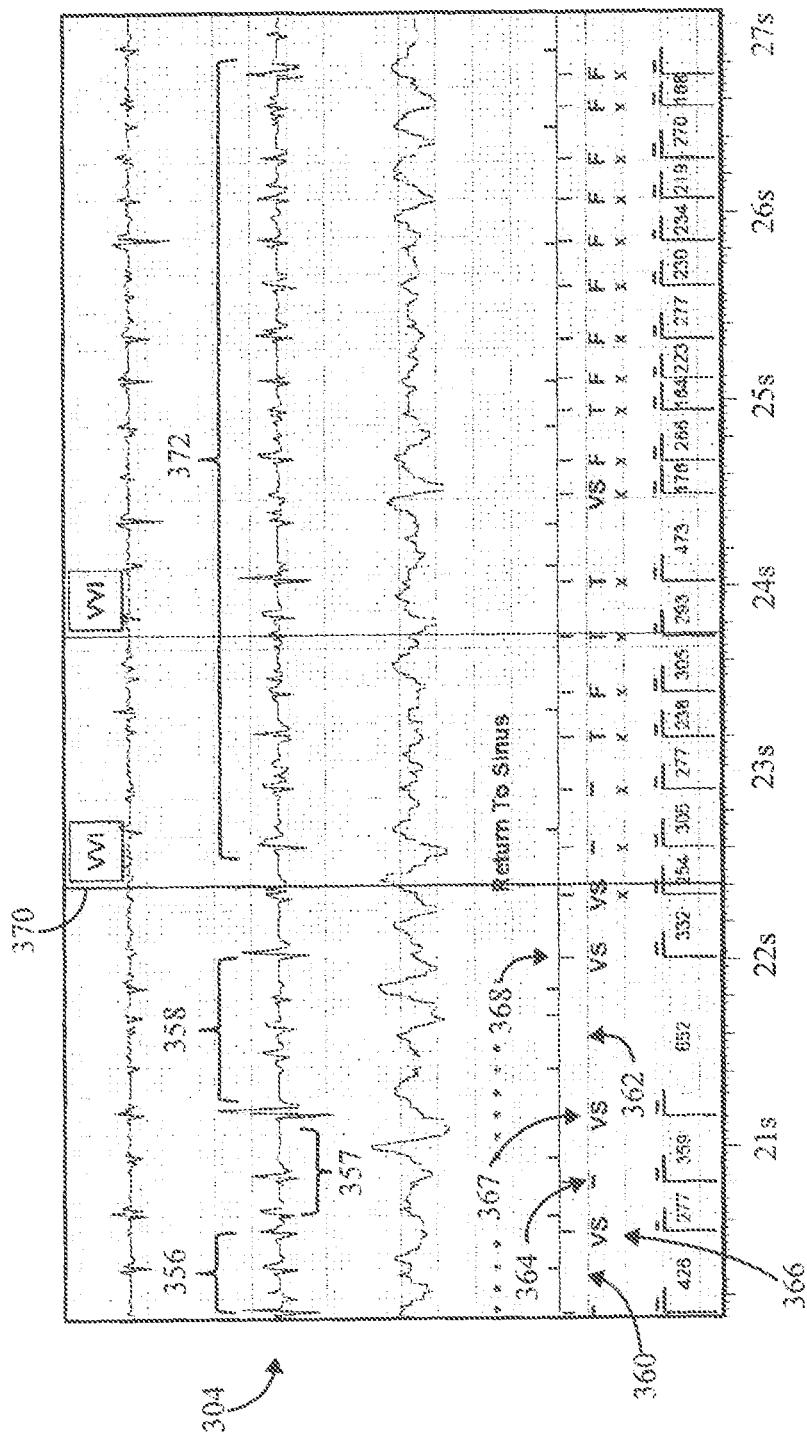
FIG. 3D illustrates panels of electrocardiogram (EGM) cardiac signals sensed over corresponding sensing vectors by an IMD in accordance with embodiments herein.

In FIG. 3D, the ventricular sensing channel 304 continues to display abnormal signals. However, the NF signals in certain segments, such as segments 356-358, are either afforded no label (as noted in the blank regions 360, 362) or are afforded an indeterminate event marker 364. The IMD goes on to identify normal ventricular sensed events at sinus event markers 366-368 which leads to a subsequent declaration that the heart behavior has returned to a sinus behavior at 370. Following the declaration of sinus behavior 370, the ventricular sensing channel 304 continues to exhibit (over segment 372) varying intervals that lead to identification of tachycardia event markers, fibrillation event markers and indiscriminate event markers over the interval between 22.5 seconds and 27 seconds within the EGM trace).

In accordance with embodiments herein, the processors of the IMD and/or external device monitor the event markers within the event marker channel 308 (e.g., at 206 in FIG. 2A). From the monitoring operation, the processors detect a presence of a candidate arrhythmia condition, such as by expiration of the arrhythmia testing timer and/or searching for event marker patterns over the series of event markers in the event marker channel 308. The search at 206-208 in FIG. 2A would identify a candidate arrhythmia from the pattern of event markers illustrated in the event marker channel 308 over the EGM panels in FIGS. 3B and 3C. At 214, the processors would determine that instability criteria are satisfied as a sufficient number of cycles or time has passed without meeting a sinus or arrhythmia detection criteria. At 216, the processors would analyze the far field sensing channel 306 and FIG. 3B and determine that the FF sensing channel 306 includes an under-detected arrhythmia indicator as at least segment 336 did not result in identification of a ventricular sensed event. At 218, the processors would declare an arrhythmia, realizing that the far field sensing channel 306 is exhibiting an under-sensing condition, thereby indicating polymorphic VT/VF. At 222, the IMD would skip directly to shocking as polymorphic VT and VF are not typically amenable to ATP. Constantly, the ATP therapy at 342 would be skipped.

In the event that ATP therapy was delivered as at 342 and/or the shock was not effective, the process of FIG. 2A would identify the candidate arrhythmia condition exhibited at segment 344 (FIG. 3C). The processors would again declare an arrhythmia and deliver a therapy at 218, 222. Optionally, at 220, the processors may extend a parameter determining a number of cycles to track before declaring a return to sinus condition. Optionally, at 370, when the IMD declares a return to sinus condition, the IMD starts a redetection timer and monitors for new candidate arrhythmia conditions. When a certain sequence of indeterminate, Tach, and/or Fib events occur, the FF sensing is checked again and if the under-detected arrhythmia criteria are met, the process may change the VT/VF sensing and/or therapy parameters changed, declare an arrhythmia episode and/or deliver therapy.

FIG. 2B illustrates a process for tracking occurrence of new arrhythmia episodes within a redetection time period of one another in accordance with embodiments herein. As noted above, the operations of FIG. 2B may be performed in parallel with the operations of FIG. 2A. At 250, the one or more processors determine whether an end condition has been declared for a candidate arrhythmia condition. For example, the processors may determine whether the arrhythmia detection algorithm has declared the end of an arrhythmia episode. If so, flow moves to 252. Otherwise, flow continues to 254. At 252, the one or more processors start a redetection timer that is set for a predetermined period of time (e.g., 30 seconds). The redetection timer defines an interval, following the end of a first arrhythmia episode, during which the process monitors for onset of a second/new arrhythmia episode. Occurrence of a new arrhythmia episode within the redetection timer interval is indicative of under detection of an arrhythmia.

At 254, the one or more processors determine whether onset has occurred for a new arrhythmia episode that was detected before expiration of the redetection timer. When a new arrhythmia episode is declared before expiration of the redetection timer, flow returns to 214 in FIG. 2A. Alternatively, when no new arrhythmia episode is detected during the redetection timer, flow continues to 256. At 256, the one or more processors determine whether the redetection timer has expired. When the redetection timer expires, flow moves to 258. At 258, the redetection timer is reset. Thereafter, the process of FIG. 2B returns to the beginning of the process of FIG. 2A where additional near field and far field cardiac signals are sensed.

In accordance with the foregoing process of FIG. 2B, embodiments herein start a timer in response to an end condition declared for the candidate arrhythmia condition, identify when a second candidate arrhythmia condition is declared before the timer expires, and based on the identifying operation, analyze the FF signals for the presence of an under-detected arrhythmia indicator.

External Device

Figure 4:
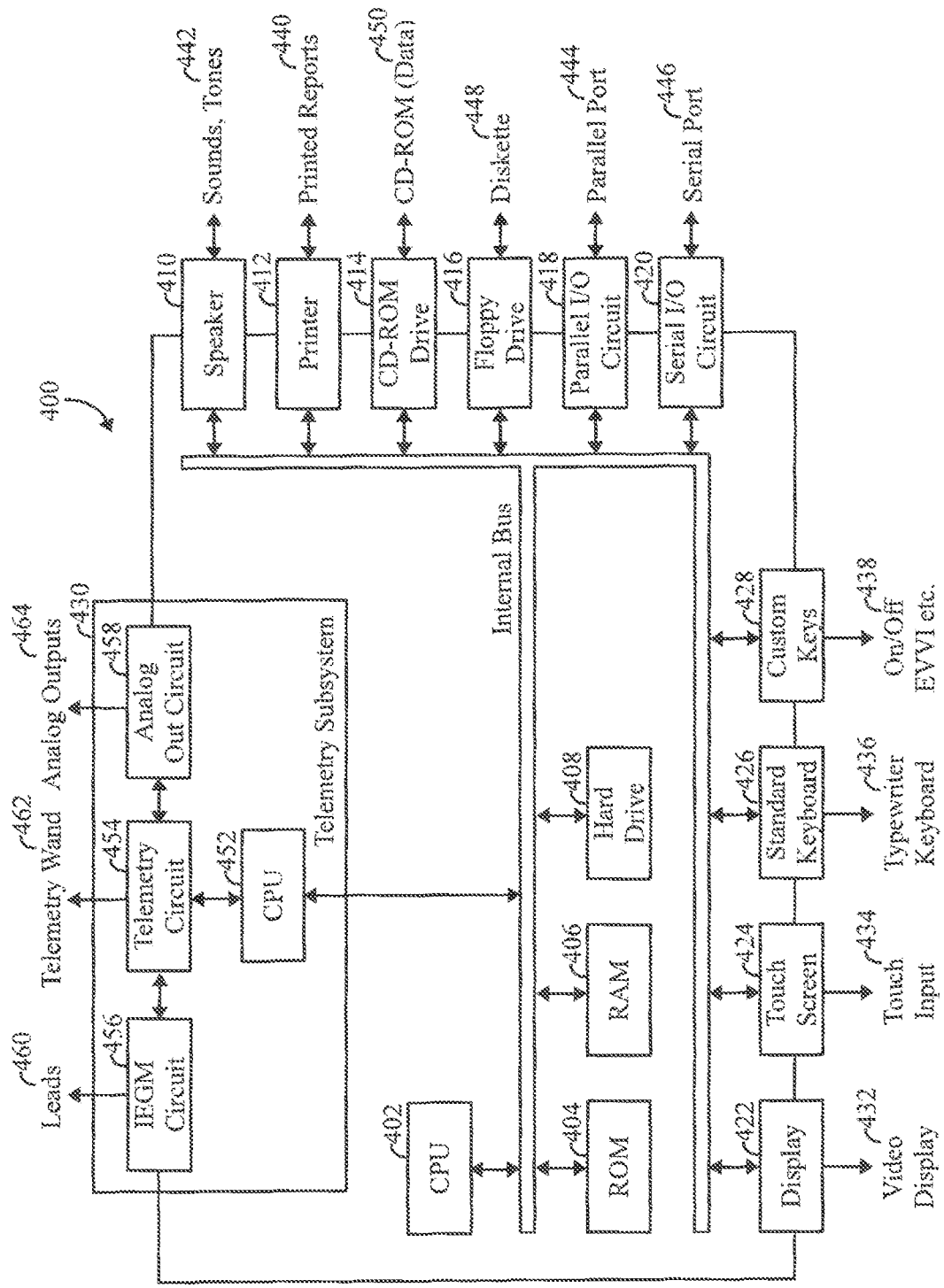
FIG. 4 illustrates a functional block diagram of the external device that is operated in accordance with the processes described herein and to interface with implantable medical devices as described herein.

FIG. 4 illustrates a functional block diagram of the external device 400 that is operated in accordance with the processes described herein and to interface with implantable medical devices as described herein. The external device 400 may be a workstation, a portable computer, an IMD programmer, a PDA, a cell phone and the like. The external device 400 includes an internal bus that connects/interfaces with a Central Processing Unit (CPU) 402, ROM 404, RAM 406, a hard drive 408, the speaker 410, a printer 412, a CD-ROM drive 414, a floppy drive 416, a parallel I/O circuit 418, a serial I/O circuit 420, the display 422, a touch screen 424, a standard keyboard connection 426, custom keys 428, and a telemetry subsystem 430. The internal bus is an address/data bus that transfers information between the various components described herein. The hard drive 408 may store operational programs as well as data, such as waveform templates and detection thresholds.

The CPU 402 typically includes a microprocessor, a microcontroller, or equivalent control circuitry, designed specifically to control interfacing with the external device 400 and with the IMD 100. The CPU 402 performs operations discussed herein in connection with FIGS. 2-3D. The CPU 402 may include RAM or ROM memory, logic and timing circuitry, state machine circuitry, and I/O circuitry to interface with the IMD 100. The display 422 (e.g., may be connected to the video display 432). The touch screen 424 may display graphic information relating to the IMD 100. The display 422 displays various information related to the processes described herein. The touch screen 424 accepts a user's touch input 434 when selections are made. The keyboard 426 (e.g., a typewriter keyboard 436) allows the user to enter data to the displayed fields, as well as interface with the telemetry subsystem 430. Furthermore, custom keys 428 turn on/off 438 (e.g., EVVI) the external device 400. The printer 412 prints copies of reports 440 for a physician to review or to be placed in a patient file, and speaker 410 provides an audible warning (e.g., sounds and tones 442) to the user. The parallel I/O circuit 418 interfaces with a parallel port 444. The serial I/O circuit 420 interfaces with a serial port 446. The floppy drive 416 accepts diskettes 448. Optionally, the floppy drive 416 may include a USB port or other interface capable of communicating with a USB device such as a memory stick. The CD-ROM drive 414 accepts CD ROMs 450.

The telemetry subsystem 430 includes a central processing unit (CPU) 452 in electrical communication with a telemetry circuit 454, which communicates with both an IEGM circuit 456 and an analog out circuit 458. The circuit 456 may be connected to leads 460. The circuit 456 is also connected to the implantable leads to receive and process IEGM cardiac signals as discussed above. Optionally, the IEGM cardiac signals sensed by the leads may be collected by the IMD 100 and then transmitted, to the external device 400, wirelessly to the telemetry subsystem 430 input.

The telemetry circuit 454 is connected to a telemetry wand 462. The analog out circuit 458 includes communication circuits to communicate with analog outputs 464. The external device 400 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 400 to the IMD 100.

Implantable Medical Device

Figure 5:
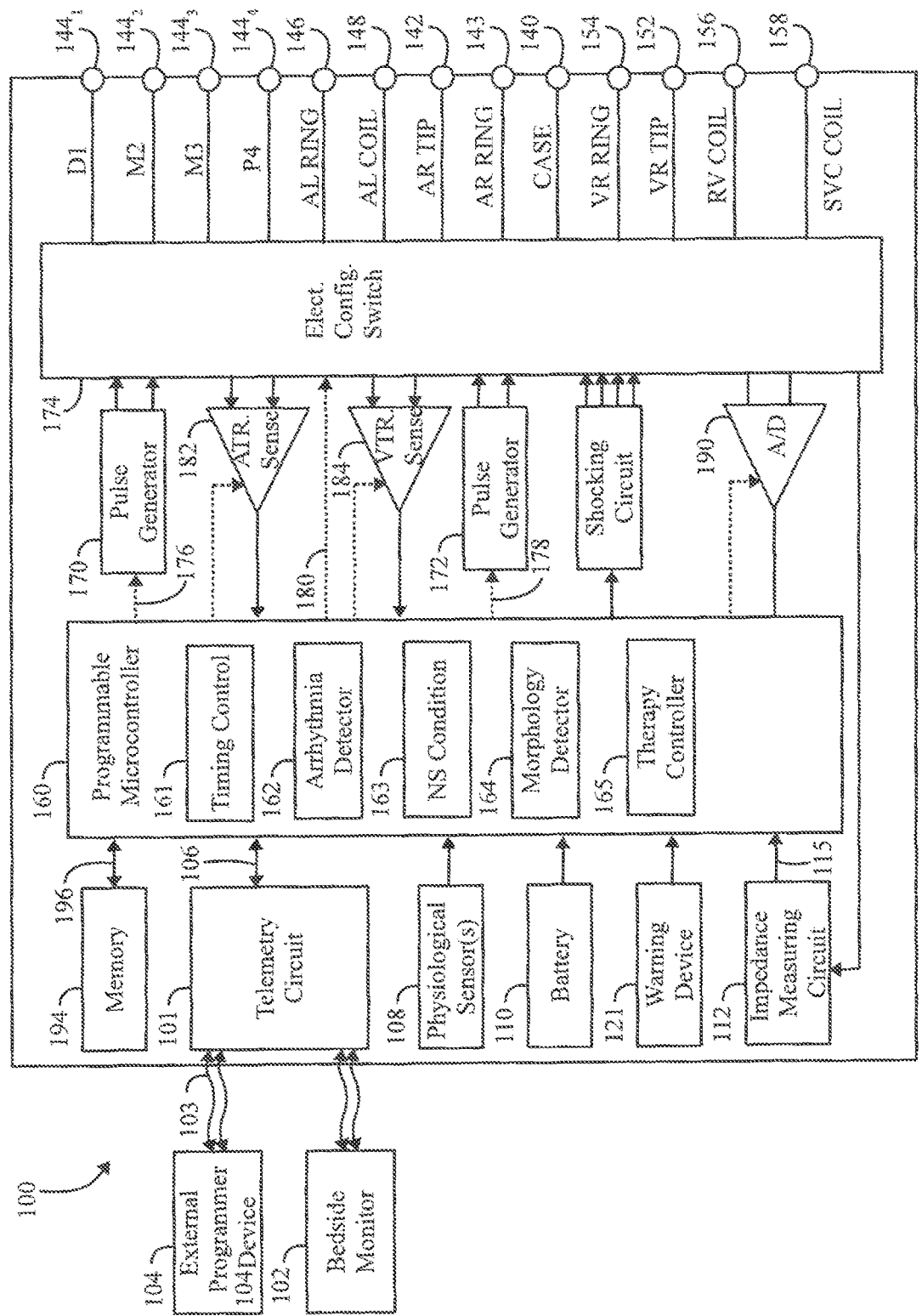
FIG. 5 illustrates a simplified block diagram of internal components of the IMD in accordance with embodiments herein.

FIG. 5 illustrates a simplified block diagram of internal components of the IMD 100 (e.g., IMD) according to an embodiment. While a particular IMD 100 is shown, it is for illustration purposes only. One of skill in the art could readily duplicate, eliminate, or disable the appropriate circuitry in any desired combination to provide a device capable of treating the appropriate chamber(s) with cardioversion, defibrillation, and pacing stimulation. The housing/CAN 140 for IMD 100 may be programmably selected to act as the anode for at least some unipolar modes. The CAN 140 may further be used as a return electrode alone or in combination with one or more of the coil electrodes 128, 136, and 138 (all shown in FIG. 1) for shocking purposes.

The IMD 100 further includes a connector (not shown) having a plurality of terminals, 142, 143, 144$_1$-144$_4$, 146, 148, 152, 154, 156, and 158 (shown schematically and, for convenience, with the names of the electrodes to which they are connected). As such, to achieve right atrial (RA) sensing and pacing, the connector includes at least an RA tip terminal ($A_R$ TIP) 142 adapted for connection to the atrial tip electrode 122 (shown in FIG. 1) and an RA ring ($A_R$ RING) electrode 143 adapted for connection to the RA ring electrode 123 (shown in FIG. 1). To achieve left chamber sensing, pacing, and shocking, the connector includes an LV tip terminal 144$_1$ adapted for connection to the D1 electrode and additional LV electrode terminals 144$_2$, 144$_3$, and 144$_4$ adapted for connection to the M2, M3, and P4 electrodes, respectively, of the quadripolar LV lead 124 (shown in FIG. 1). The connector also includes an LA ring terminal ($A_L$ RING) 146 and an LA shocking terminal ($A_L$ COIL) 148, which are adapted for connection to the LA ring electrode 127 (shown in FIG. 1) and the LA coil electrode 128 (shown in FIG. 1), respectively. To support right chamber sensing, pacing, and shocking, the connector further includes an RV tip terminal ($V_R$ TIP) 152, an RV ring terminal ($V_R$ RING) 154, an RV coil terminal (RV COIL) 156, and an SVC coil terminal (SVC COIL) 158, which are adapted for connection to the RV tip electrode 132, the RV ring electrode 134, the RV coil electrode 136, and the SVC coil electrode 138 (all four electrodes shown in FIG. 1), respectively.

The IMD 100 includes a programmable microcontroller 160 (also referred to herein as a control unit or controller) that Includes a microprocessor or equivalent control circuitry, designed specifically for controlling the delivery of stimulation therapy. The microcontroller 160 may further include RAM or ROM memory, logic and timing circuitry, state machine circuitry, and/or I/O circuitry. The microcontroller 160 includes the ability to process or monitor input signals (data) as controlled by a program code stored in a designated block of memory. The details of the design and operation of the microcontroller 160 are not critical to the invention. Rather, any suitable microcontroller 160 may be used that carries out the functions described herein. Among other things, the microcontroller 160 receives, processes, and manages storage of digitized cardiac data sets from the various sensors and electrodes.

A pulse generator 170 and a pulse generator 172 are configured to generate and deliver a pacing pulse from at least one RV or RA pacing site, such as at one or more pacing sites along the RA lead 120, the RV lead 130, and/or the LV lead 124 (all three leads shown in FIG. 1). The pulse generators 170, 172 are controlled by the microcontroller 160 via appropriate control signals 176, 178, respectively, to trigger or inhibit the stimulation pulses, including the timing and output of the pulses. The electrode configuration switch 174 may include a plurality of switches for connecting the desired electrodes to the appropriate I/O circuits, thereby providing complete electrode programmability. Accordingly, the switch 174, in response to a control signal 180 from the microcontroller 160, controls the polarity of the stimulation pulses (e.g., unipolar, bipolar, etc.) by selectively actuating the appropriate combination of switches (not shown) as is known in the art. The switch 174 also switches among the various LV electrodes 126 to select the channels (e.g., vectors) to deliver and/or sense one or more of the pacing pulses. As explained herein, the switch 174 couples multiple LV electrode terminals 144$_1$-144$_4$ correspond to cathodes when connected to the pulse generator 172.

Atrial sensors or sensing circuits 182 and ventricular sensors or sensing circuits 184 may also be selectively coupled to the RA lead 120, the LV lead 124, and/or the RV lead 130 (all three leads shown in FIG. 1) through the switch 174. The atrial and ventricular sensors 182 and 184 have the ability to detect the presence of cardiac activity in each of the four chambers of the heart 105 (shown in FIG. 1). For example, the ventricular sensor 184 is configured to sense LV activation events at multiple LV sensing sites, where the activation events are generated in response to a pacing pulse or an intrinsic event. In an embodiment, the ventricular sensor 184 senses along at least four sensing vectors, each sensing vector utilizing a sensing electrode in the left ventricle.

The atrial sensing circuits 182 and ventricular sensing circuits 184 are coupled to a lead, the lead having electrodes to sense near field (NF) and far field (FF) signals between first and second combinations of electrodes. The atrial sensing circuits 182 and ventricular sensing circuits 184 may include dedicated sense amplifiers, multiplexed amplifiers, or shared amplifiers. The switch 174 determines the "sensing polarity" or sensing vector of the cardiac signal by selectively opening and/or closing the appropriate switches, as is known in the art. In this way, a clinician may program the sensing polarity independent of the stimulation polarity.

Cardiac signals are also applied to the inputs of an analog-to-digital (A/D) data acquisition system 190. The A/D data acquisition system 190 is configured to acquire intracardiac electrogram (EGM) signals, convert the raw analog data into a digital signal, and store the digital signals for later processing and/or telemetric transmission. The telemetric transmission may be to an external programmer device 104, a bedside monitor, cellular phone, tablet device and/or a personal advisory module (PAM) 102. The data acquisition system 190 may be operatively coupled to the RA lead 120, the LV lead 124, and the RV lead 130 (all three leads shown in FIG. 1) through the switch 174 to sample cardiac signals across any pair of desired electrodes.

The microcontroller 160 includes timing control module 161 to control the timing of the stimulation pacing pulses, including, but not limited to, pacing rate, atrio-ventricular delay, Interatrial conduction delay, interventricular conduction delay, and/or intraventricular delay. The timing control module 161 can also keep track of the timing of refractory periods, blanking intervals, noise detection windows, evoked response detection windows, alert intervals, marker channel timing, etc., which is known in the art.

The microcontroller 160 further includes an arrhythmia detector 162 for operating the system as an implantable cardioverter/defibrillator device. The detector 162 apply an arrhythmia detection algorithm to the NF signals for identifying events within the NF signal and designate events marker based thereon. The detector 162 determines desirable times to administer various therapies. For example, the detector 162 may detect the occurrence of an arrhythmia and automatically control the application of an appropriate electrical shock therapy to the heart aimed at terminating the detected arrhythmia.

The microcontroller 160 includes a therapy controller 165 to manage pacing therapy, which can be performed in conjunction with CRT pacing. As an example, the therapy controller 165 may control the pulse generator 172 to simultaneously deliver a pacing pulse over a select pacing vector. The arrhythmia detector 162, morphology detector 164, and/or therapy controller 165 may be implemented in hardware as part of the microcontroller 160, or as software/firmware instructions programmed into the system and executed on the microcontroller 160 during certain modes of operation. The therapy controller 165 also controls delivery of CRT pacing pulses to synchronize the contractions of the right and left ventricles. The therapy controller 165 controls the number, timing, and output of the CRT pacing pulses delivered during each cardiac cycle, as well as over which pacing vectors the pacing pulses are to be delivered.

The microcontroller 160 may additionally include an under-detected potential arrhythmia condition detector 163 that perform the operations described herein. The under-detected potential arrhythmia condition detector 163 monitors the event markers to under-detected arrhythmia condition comprises an under-detected arrhythmia or over-sensing. The under-detected potential arrhythmia condition detector 163, in response to detection of the candidate arrhythmia condition, analyzes the FF signals for a presence of an under-detected arrhythmia indicator. The under-detected potential arrhythmia condition detector 163 delivers an arrhythmia therapy based on the presence of the under-detected arrhythmia indicator in the FF signals and the candidate under-detected arrhythmia condition in the NF signals. Optionally, the under-detected potential arrhythmia condition detector 163 may be further configured to set the under-detected arrhythmia indicator positive based on a level of cardiac activity, wherein the under-detected arrhythmia indicator indicates that the FF signal lacks the level of cardiac activity to satisfy a threshold. Optionally, the under-detected potential arrhythmia condition detector 163 may be configured to set the under-detected arrhythmia indicator positive when at least one of i) an amount of time for which the FF signal does not include cardiac activity, ii) a number of cardiac cycles for which the FF signal does not include cardiac activity, or iii) the signals are of a certain amplitude or shape. Optionally, the event marker patterns may comprise a first event marker pattern indicative of an under-detected arrhythmia, and a second event marker pattern Indicative of over-sensing. Optionally, the under-detected potential arrhythmia condition detector 163 may be configured to perform the monitor and analyze operations in connection with NF signals that the arrhythmia detection algorithm declared to not exhibit an arrhythmia episode. Optionally, the under-detected potential arrhythmia condition detector 163 may be configured to determine whether event markers exhibit a first event marker pattern indicative of an arrhythmia and determine whether event markers exhibit a second event marker pattern indicative of over-sensing. Optionally, the under-detected condition detector 163 may be configured to determine whether an arrhythmia testing timer has expired, the arrhythmia testing timer representing a predetermined maximum period of time to elapse since the arrhythmia detection algorithm began attempting to identify an arrhythmia.

The microcontroller 160 is further coupled to a memory 194 by a suitable data/address bus 196. The programmable operating parameters used by the microcontroller 160 are stored in the memory 194 and modified, as required, in order to customize the operation of IMD 100 to suit the needs of a particular patient. Such operating parameters define, for example, the amplitude or magnitude of the generated pacing pulses, wave shape, pulse duration, and/or vector (e.g., including electrode polarity) for the pacing pulses. Other pacing parameters may include base rate, rest rate, and/or circadian base rate. The memory 194 also stores conduction patterns or morphologies, as well as other data and information described herein. The memory 194 stores the NF and FF signals.

Optionally, the operating parameters of the implantable IMD 100 may be non-invasively programmed into the memory 194 through a telemetry circuit 101 in telemetric communication with an external programmer device 104 or a bedside monitor 102, such as a programmer, trans-telephonic transceiver, cellular phone or a diagnostic system analyzer. The telemetry circuit 101 is activated by the microcontroller 160 through a control signal 106. The telemetry circuit 101 may allow IEGMs, conduction patterns, morphologies as well as other data and information described herein, and status information relating to the operation of IMD 100 (contained in the microcontroller 160 or the memory 194) to be sent to the external programmer device 104 and/or bedside monitor 102, and vice-versa, through an established communication link 103. An internal warning device 121 may be provided for generating perceptible warning signals to a patient and/or caregiver via vibration, voltage, sounds or other methods.

IMD 100 further includes an accelerometer or other physiologic sensor 108. The physiologic sensor 108 is commonly referred to as a "rate-responsive" sensor because it may be used to adjust the pacing stimulation rate according to the exercise state (e.g., heart rate) of the patient. However, the physiologic sensor 108 may further be used to detect changes in cardiac output, changes in the physiological condition of the heart, and/or diurnal changes in activity (e.g., detecting sleep and wake states and arousal from sleep).

The IMD 100 additionally includes a battery 110, which provides operating power to all of the circuits therein. The makeup of the battery 110 may vary depending on the capabilities of IMD 100. If the system only provides low voltage therapy (e.g., for repetitive pacing pulses), a lithium iodine or lithium copper fluoride cell may be utilized. For a IMD that employs shocking therapy, the battery may be configured to be capable of operating at low current drains for long periods and then providing high-current pulses (for capacitor charging) when the patient requires a shock pulse. The battery 110 may also be configured to have a predictable discharge characteristic so that elective replacement time can be detected.

Optionally, the IMD 100 includes an impedance measuring circuit 112, which is enabled by the microcontroller 160 via a control signal 115. Uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 112 is coupled to the switch 174 so that any desired electrode may be used.

The above described implantable medical device 100 was described as an exemplary IMD. One of ordinary skill in the art would understand that one or more embodiments herein may be used with alternative types of implantable devices. Accordingly, embodiments should not be limited to using only the above described device 100.

CLOSING STATEMENTS

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and Illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which Illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other Information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional Items.

It is to be understood that the above description is Intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method, comprising:
   under control of one or more processors within an implantable medical device (IMD),
   sensing near field (NF) and far field (FF) signals between first and second combinations of electrodes coupled to the IMD for multiple beats;
   applying an arrhythmia detection algorithm to the NF signals for identifying events within the NF signal and designate multiple event markers based thereon;
   monitoring the multiple event markers to detect a candidate arrhythmia condition in the NF signals based on the multiple event markers for the corresponding multiple beats;
   identifying a type of the candidate arrhythmia condition to be an under-detected arrhythmia or over-sensing based on the multiple event markers;

in response to the identification of the under-detected arrhythmia, analyzing the FF signals for a presence of an under-detected arrhythmia indicator for the multiple beats; and delivering an arrhythmia therapy based on the presence of the under-detected arrhythmia indicator in the FF signals and the identification of the under-detected arrhythmia in the NF signals.

2. The method of claim 1, further comprising setting the under-detected arrhythmia indicator positive based on a level of cardiac activity in the FF signals not satisfying a threshold.

3. The method of claim 1, further comprising setting the under-detected arrhythmia indicator positive when at least one of i) the FF signals do not include cardiac activity for a predetermined amount of time, ii) the FF signals do not include cardiac activity for a predetermined number of cardiac cycles, or iii) the NF signal is not characteristic of sinus cardiac activity.

4. The method of claim 1, wherein the monitoring operation comprises searching for event marker patterns exhibited over a series of the multiple event markers, the identifying operation comprises identifying the type of candidate arrhythmia condition based on the event marker patterns.

5. The method of claim 4, wherein the event marker patterns comprise a first event marker pattern indicative of the under-detected arrhythmia, and a second event marker pattern indicative of the over-sensing.

6. The method of claim 1, wherein the monitoring comprises incrementing and decrementing a counter based on the event markers that label different cardiac events within the NF signals.

7. The method of claim 1, wherein the monitoring and analyzing operations are performed in connection with NF signals that the arrhythmia detection algorithm declared to not exhibit an arrhythmia episode.

8. The method of claim 1, wherein the monitoring further comprises determining whether event markers exhibit a first event marker pattern indicative of the under-detected arrhythmia and determining whether the event markers exhibit a second event marker pattern indicative of the over-sensing.

9. The method of claim 1, further comprising determining whether an instability criteria is satisfied by the NF signals, the instability criteria defining an unstable condition in which the NF signal is not classified, by the arrhythmia detection algorithm, as a sinus episode or arrhythmia episode, for a predetermined number of cardiac cycles and/or period of time.

10. The method of claim 9, wherein the instability criteria representing at least one of i) a condition in which a predetermined number of cardiac cycles have occurred without reaching a detection criteria or ii) a condition in which a predetermined time period has passed without reaching a detection criteria.

11. The method of claim 1, further comprising:
starting a timer in response to an end condition declared for the candidate arrhythmia condition;
identifying when a second candidate arrhythmia condition is declared before the timer expires; and
based on the identifying, performing the analyzing the FF signals for the presence of an under-detected arrhythmia indicator.

12. A system comprising:
electrodes;
an implantable medical device (IMD) coupled to the electrode, the IMD configured to sense near field (NF) and far field (FF) signals between the electrodes for multiple beats;
memory to store the NF and FF signals and to store program instructions; and
a processor that, when executing the program instructions, is configured to:
apply an arrhythmia detection algorithm to the NF signals for identifying events within the NF signal and designate multiple event markers based thereon;
monitor the multiple event markers to detect a candidate arrhythmia condition in the NF signals based on the multiple event markers for the corresponding multiple beats;
identifying a type of the candidate arrhythmia condition to be an under-detected arrhythmia or over-sensing based on the multiple event markers;
in response to the identification of the under-detected arrhythmia, analyze the FF signals for a presence of an under-detected arrhythmia indicator; and
deliver an arrhythmia therapy based on the presence of the under-detected arrhythmia indicator in the FF signals and the identification of the under-detected arrhythmia in the NF signals.

13. The system of claim 12, wherein the processor is further configured to set the under-detected arrhythmia indicator positive based on a level of cardiac activity in the FF signals not satisfying a threshold.

14. The system of claim 12, wherein the processor is further configured to set the under-detected arrhythmia indicator positive when at least one of i) the FF signals do not include cardiac activity for a predetermined amount of time, ii) the FF signals do not include cardiac activity for a predetermined number of cardiac cycles, or iii) the FF signal is not characteristic of sinus cardiac activity.

15. The system of claim 12, wherein the processor is configured to determine whether a series of the multiple event markers exhibits a first event marker pattern indicative of the under-detected arrhythmia or a second event marker pattern indicative of the over-sensing.

16. The system of claim 12, wherein the processor is further configured to perform the monitor and analyze operations in connection with NF signals that the arrhythmia detection algorithm declared to not exhibit an arrhythmia episode.

17. The system of claim 12, wherein the processor is further configured to determine whether the multiple event markers exhibit a first event marker pattern indicative of an arrhythmia.

18. The system of claim 12, further comprising: a housing, wherein the processor and memory are held within the housing of the IMD, the processor further configured to adapt at least one parameter of the arrhythmia therapy based on the presence of the under-detected arrhythmia indicator in the FF signals.

19. The system of claim 12, wherein the processor is further configured to determine whether an arrhythmia testing timer has expired, the arrhythmia testing timer representing a predetermined maximum period of time to elapse since the arrhythmia detection algorithm began attempting to identify an arrhythmia.

20. The system of claim 12, wherein electrodes include first and second combinations of the electrodes, the IMD configured to sense near field (NF) and far field (FF) signals between the first and second combinations of the electrodes, respectively.

21. The method of claim 1, wherein the processor is configured to perform the apply, monitor, analyze and deliver operations in real time while a patient is experiencing an arrhythmia.

22. The system of claim 12, wherein the sensing, applying, monitoring, analyzing and delivering are performed in real time while a patient is experiencing an arrhythmia.

23. The method of claim 1, wherein the candidate arrhythmia condition comprising the under-detected arrhythmia, and not the over-sensing.

24. The method of system of claim 12, wherein the candidate arrhythmia condition comprising the under-detected arrhythmia, and not the over-sensing.

* * * * *